United States Patent [19]

Brine

[11] Patent Number: 5,075,115

[45] Date of Patent: Dec. 24, 1991

[54] PROCESS FOR POLYMERIZING POLY(LACTIC ACID)

[75] Inventor: Charles J. Brine, Princeton, N.J.

[73] Assignee: FMC Corporation, Philadelphia, Pa.

[21] Appl. No.: 620,247

[22] Filed: Nov. 30, 1990

Related U.S. Application Data

[63] Continuation of Ser. No. 503,397, Apr. 2, 1990, abandoned.

[51] Int. Cl.$^5$ .................. A61K 9/14; A61K 9/22; A61K 9/52
[52] U.S. Cl. .................. 424/486; 424/422; 424/426; 424/484; 514/964
[58] Field of Search .......... 424/426, 486, 422, 78, 424/484; 514/826, 964; 528/354

[56] References Cited

U.S. PATENT DOCUMENTS 4,728,721 3/1988 Yamamoto et al. ............ 528/354 X

FOREIGN PATENT DOCUMENTS 60-181029A 9/1985 Japan .

OTHER PUBLICATIONS

Mark et al., Collected Papers of Wallace Hume Carothers on High Polymeric Substances, Interscience Publishers, Inc. (1940), pp. 152-153.

*Primary Examiner*—Thurman Page
*Assistant Examiner*—Robert H. Harrison
*Attorney, Agent, or Firm*—R. E. Elden; P. C. Baker

[57] ABSTRACT

A process is provided for the condensation polymerizing lactic acid to a polymer with a weight average molecular weight of 2,500 to 4,500 containing less than 4% lactide and for a controlled release dosage form comprising a pharmaceutically active ingredient in a matrix of poly(lactic acid) and its copolymers with glycolic acid, valerolactone, $\epsilon$-caprolactone, $\epsilon$-decalactone, hydroxybutyric acid, $\beta$-hydroxyvaleric acid and dioxanone.

3 Claims, No Drawings

PROCESS FOR POLYMERIZING POLY(LACTIC ACID)

This is a continuation of U.S. Pat. Application Ser. No. 503,397 filed Apr. 2, 1990, now abandoned.

FIELD OF THE INVENTION

This invention relates to a process for polymerizing poly(latic acid) with a molecular weight of 2,500 to 4,500 containing less than 4% lactide and to a poly(latic acid) matrix dosage formulation, such as a tablet, a bead or the like, with a controlled and delayed release of the active ingredient.

BACKGROUND OF THE INVENTION

Solid pharmaceutically active preparations which provide sustained release of an active ingredient over a long period of time are desirable in that they ensure a constant concentration of active ingredient in the body. These delayed release forms make it possible to reduce the number of doses of the drug to be administered and thus simplify the treatment plan. Usually delayed release tablets and capsules are provided with a coating which regulates the release of active ingredient.

One disadvantage of relying on coatings for the delayed release property is that any inadvertent puncture of the coating or division of the tablet critically affects the coating integrity or the total surface area of the tablet. As a result, the characteristics of the release of the active ingredient are significantly altered, so that, in many cases, the tablets no longer have the therapeutically useful delayed and continuous release profile of an active ingredient.

Microencapsulated formulations do not wholly overcome the problem of controlled release because the film-forming agent frequently forms a continuous phase after a period of time, making it impossible to maintain reproducible release rates. U.S. Pat. No. 4,716,041 to Kjornaes et al. teaches a microencapsulated formulation of a first, inner film-forming coating, a second, outer film coating. The coated formulations are subsequently heated to permit the inner film-forming coating to form a continuous phase with uniform diffusion characteristics with time. Such a multiple coating process adds to the expense of a formulation and does not overcome the problem of coating integrity for tablets, caplets and other dosage forms. Further, the heating step may adversely affect the active ingredient.

Orally administerable pharmaceutical preparations are known in which the active ingredient is embedded in a polymer or matrix. The matrix slowly dissolves or erodes to release the pharmaceutically active ingredient. The feed formulations of pharmaceutical preparations of this kind are normally produced by dissolving the active ingredient together with a polymer in a solvent, then evaporating the solvent and granulating the solid mixture. Frequently the removal of the solvent and the granulation are carried out in a single operation by spray drying Pharmaceutical preparations of this type are intended for the purpose of distributing the active ingredient in a finely dispersed form through the polymer and increasing the surface area of the substance which is to be dissolved, so as to accelerate and not delay the dissolution.

U.S. Pat. No. 4,547,359 teaches that a divisible polyacrylate-based tablet may be formed of a compressed composition comprising a finely divided polyacrylate material having the active ingredient incorporated therein in molecular dispersion, and conventional tablet excipients. However, the patent teaches it is particularly important to use a specific acrylate polymerized by emulsion polymerization and having a particle size of about 140 nm. Polyacrylates prepared by other methods, such as by solution or block polymerization, are unsuitable for purposes of the invention. In order to ensure a delayed release of the active ingredient, the active ingredient embedded in the polyacrylate material should have diffusion coefficients of $10^{-5}$ to $10^{-7}$ cm$^2$ per hour. However, it is undesirable to restrict the pharmaceutically active compounds to such a narrow range of diffusion coefficients.

U.S. Pat. No. 4,692,337 to Ukigaya et al. teaches that prior art formulations based on a water-insoluble or slightly water soluble matrix have two disadvantages, the weight percentage of the matrix material must be 50% or more of the total weight, and that the rate of release of the medication rapidly decreases with time. Instead, the patent teaches dry mixing 100 parts of theophylline with 5 to 200 parts of ethyl cellulose and compressing the mixture into tablets.

Polylactic acid with a weight average molecular weight of 30,000 or more (PLA) is a well-known biologically compatible, water insoluble polymeric body employed for the sustained release of pharmaceutically active ingredients. On the other hand, it is generally recognized that polylactic acid made by condensation of lactic acid (weight molecular weight of a few thousand) has generally unsatisfactory physical properties. U.S. Pat. No.4,357,312 teaches an implantable matrix suitable for dispensing pharmaceutically active ingredients in which the pharmaceutically active ingredient is dissolved in a mixture of high molecular weight polylactic acid (weight average molecular weight greater than 30,000), solvent and water. Freezing the water creates channels, and subsequent drying removes the solvent and water. The freezing conditions must be carefully controlled to make the release of the pharmaceutically active ingredient uniform.

U.S. Pat. No.4,659,588 discloses bioerodable polymers useful to form coatings including polycarboxylic acids, polyamides, polylactic acid, polyglycolic acid and the like.

U.S. Pat. No.4,666,702 teaches a drug delivery tablet containing a central core and a coating which is a thermoplastic polymer, optionally, high molecular weight polylactic acid, nylon, polyglycolic acid and the like.

U.S. Pat. No.4,652,441 teaches a microcapsule or bead suitable for controlled release of a water soluble pharmaceutically active ingredient including an oil layer thickened with high molecular weight polylactic acid.

PCT Application Serial No. U.S. 88/04208 claims a method for preparing a sustained release dosage or delivery form by blending a dosage amount of a functionally active ingredient, an excipient and a high molecular weight polymer having a glass transition temperature of about 30° C. to about 150° C., preferably about 40° C. to 100° C., into a feed formulation, and maintaining the shaped form at or above the glass transition temperature of the polymer for a sufficient time to provide a dosage form having controlled, sustained release of the functionally active ingredient when the dosage form is administered. However, many functionally active ingredients decompose on heating so that this method is limited to heat stable functionally active ingredients.

SUMMARY OF THE INVENTION

The present invention is a process for polymerizing lactic acid to poly(lactic acid) comprising the steps of:

(a) heating lactic acid in a inert atmosphere to about 110° C. at approximately 101 kPa, (b) advancing the temperature to about 120° C., (c) maintaining the temperature between about 120° and 140° at a pressure of about 80 kPa a sufficient time to remove about 52% of the theoretical amount of water, and subsequently advancing the temperature to 180° C. to 190° C. while reducing the pressure to about 10 kPa, (d) maintaining the temperature and pressure at about 190° C. and 10 kPa for a time sufficient to remove about 92% of the residual water, and (e) reducing the pressure to about 400 Pa while maintaining the temperature at least about 180° C. for a time sufficient to remove about 98% of the theoretical water and about 0.5% of the lactic acid as lactide to provide said poly(lactic acid) with a weight average molecular weight of 2500 to about 4500 and containing less than about 4% lactide.

DETAILED DESCRIPTION

The scope of the present invention is intended to include the product made by the process as well as copolymers and mixtures of polymers of glycolic acid, valerolactone, ε-caprolactone, ε-decalactone, hydroxybutyric acid, β-hydroxyvaleric acid and dioxanone and controlled release dosage forms made from said poly(lactic acid); copolymers and mixtures said controlled release dosage form comprising, a) a pharmaceutically active ingredient, and said poly(lactic acid) with a weight average molecular weight of about 2,500 to 4,500, a glass transition temperature of about 26±2° C. or less, and biodegradable copolymers or mixtures with glycolic acid, valerolactone, ε-caprolactone, ε-decalactone, L hydroxybutyric acid, β-hydroxyvaleric acid and dioxanone preferably the monomer of said poly(lactic acid) predominating in said copolymer or mixtures. Optionally, the dosage form may contain additives such as excipients, lubricants, coloring materials and the like.

Although the invention is disclosed in terms of a unitary matrix tablet, the scope of the invention is preferably intended to include any matrix form such as a tablet, bead, microcapsule, densified nonpareil, pill, granule and the like comprising 1% to 75% of a pharmaceutically active ingredient, 0% to 90% of an excipient and 5% to 75% of a polymer having a glass transition temperature from about 26° C. to about −65° C. The shaped form may subsequently be reprocessed into other dosage forms. For example, granules or small particles may be processed into capsules, or may be tabletted.

Each of the polymers are known to be biodegradable and/or bioerodable, and acceptable to control the release of pharmaceutically active compounds.

Any pharmaceutically active ingredient may be employed in the present invention together with other usual additives, such as a flavor, a fragrance or the like. Desirable functionally active pharmaceutical ingredients (alternatively called functionally active ingredients, or merely active ingredients) include vitamin compositions (for example multivitamins, multivitamins with minerals, prenatal vitamins, vitamins A and D, $B_1$, $B_2$, $B_6$, $B_{12}$, and vitamin B complex with vitamin C); analgesics (acetaminophen, aspirin, ibuprofen, ketoprofen and the like, indomethacin, naproxen, acetaminophen with codeine and acetaminophen with propoxyphene napsylate); antibiotics (erythromycin, cephalosporins, etc.); antiepileptics (phensuximide, phenytoin sodium and valproate sodium); antihistamines (chloropheniramine maleate, diphenhydramine hydrochloride, diphenhydramine, triprolidine hydrochloride); cough and cold drugs (dextromethorphan hydrobromide, ephedrine sulfate, quaifenesin, phenylpropanolamine hydrochloride, promethazine hydrochloride, and pseudoephedrine hydrochloride); cardiovascular drugs (captopril, chlorthiazide and hydrochlorthiazide, diltiazem, nadolol, papaverine hydrochloride, procainamide hydrochloride, propranolol hydrochloride, quinidine gluconate, quinidine sulfate); electrolytes (potassium chloride); gastrointestinal drugs (cimetidine, loperamide hydrochloride and ranitidine); respiratory drugs (albuterol sulfate, aminophylline, theophylline); and the like. Particularly desirable are pharmaceutically active ingredients selected from the group consisting of theophylline, quinidine sulfate, propanolol, chloropheniramine, testosterone and ethenyl estradiol.

Poly(lactic acid) with a weight average molecular weight of 2,500 to 4,500 can be prepared by condensation polymerization of lactic acid under reduced pressure. Usually an inert gas, nitrogen or argon is passed through the solution, which is heated to 120° C. at 150 torr to begin the distillation. The temperature is advanced to 180° C. slowly. After the distillation has nearly ceased, the pressure is reduced to approximately 5 torr. The heat is increased to 210° C. until the theoretical amount of water is distilled. The molten PLA product is cooled as product. However, the PLA product usually contains over 10% lactide, a lactic acid dimer.

To make poly(d,l-lactic acid) with a weight average molecular weight of 2,500 to 4,500 (preferably 3,000 to 4,000) containing less than 4% lactide (the cyclic dimer of lactic acid) the above procedure must be modified. Racemic 88% lactic acid is slowly heated to 110° C. at atmospheric pressure under an inert gas. The temperature is slowly advanced to approximately 120° C. and maintained overnight at 120–140° C. and 590 torr to remove about 52% of the theoretical amount of water.

The temperature is further advanced over 3 hours to 180–190° C. and 590 torr to remove about 52% of the theoretical amount of water.

The temperature is further advanced over 3 hours to 180–190° C. and pressure gradually reduced from approximately 200 to 80 torr. After an additional 3 hours at approximately 190° C. and 80 torr, to remove 91.8% of the theoretical water, the pressure is further reduced to 2-3 torr using a vacuum pump while the temperature remains at approximately 180° C. After 2 hours, the pressure is increased to 20 torr and the solution maintained at 200° C. to remove about 98% of the theoretical water plus ½% of the lactic acid as lactide. The syrupy product is then cooled.

To make copolymers of the above with glycolic acid, valerolactone, decalactone, or the like the same procedures are employed using the appropriate mixture of ingredients, such as, racemic lactic acid with glycolic acid, or 1(+)-lactic acid with valerolactone.

The polymer, such as poly(d,l-lactic acid) (PLA), can be introduced into the feed formulation by any convenient method such as dry mixing, wet granulation method or with a solvent system. In the latter method, the polymer is dissolved in methylene chloride and then blended into the pharmaceutically active ingredient and excipient. A lubricant or other additive such as a colorant may be optionally added.

Alternatively, the blend can be wet granulated with an aqueous latex dispersion of the polymer which is used as the binding solution. The air dried granulation is then blended with the lubricant and processed into a shaped form.

Optionally, an excipient may be employed in the feed formulation. The excipient may be employed for a single function such as a diluent, a binder, a lubricant, a disintegrant, an adsorbent, or for a combination of functions. Common excipients such as lactose, dicalcium phosphate, calcium sulfate, sugars, microcrystalline cellulose (MCC), gums, methylcellulose, starch, polyvinylpyrrolidone, clay and the like may be selected by one skilled in the art to provide their usual contribution to the dosage form. The excipient may be employed in an amount varying from 1% to about 90% by weight of the dosage form.

Particularly desirable microcrystalline cellulose excipients are marketed under the Avicel trademark by FMC Corporation. Microcrystalline cellulose is suitable for use as a binder, a diluent and as a disintegrant. The PH grades of Avicel ® microcrystalline cellulose are preferred for use in direct compression tabletting. The product is porous which permits the microcrystalline cellulose to absorb a liquid ingredient while remaining a free-flowing powder suitable to serve as a feed formulation for compression. Microcrystalline cellulose also provides an intermediate disintegration rate between the rapid disintegration rate of soluble excipients and the very slow disintegration rate of preferred insoluble excipients such as calcium sulfate and dicalcium phosphate.

A polymer, such as polylactic acid, is brittle below its glass transition temperature. The glass transition temperature ("Tg") or second order transition temperature is the temperature at which a polymer changes from a brittle material (glassy state) to a rubbery material. The glass transition temperatures of polymers vary with molecular weight. The glass transition, unlike a true thermodynamic transition, takes place over a temperature range of several degrees and is dependent upon the experimental method and the time scale used for its determination. The glass transition temperature can also vary with the additives employed such as plasticizers, lubricants and the like. Methods used to determine the glass transition temperature and the reported values for a large number of polymers are available in standard references employed by those skilled in the art. For the purpose of this invention the glass transition temperature shall include a temperature below the melting point of a polymer at which the polymer ceases to be a brittle, glassy or crystalline solid and becomes rubbery or begins to flow. The preferred polylactic acids (PLAs) having a weight average molecular weight of 2,500 to 4,500 have a Tg of less than 30° C., usually about 26±2° C. when measured by differential scanning calorimetry (DSC).

Polylactic acid is commonly known by many alternative names such as PLA; propanoic acid, 2-hydroxy-, homopolymer; lactic acid, polyesters; lactic acid, polymers; poly(lactic acid); lactic acid polymer; lactic acid homopolymer; as well as by its CAS registration number 26100-51-6. As lactic acid is optically active the above list may be multiplied by the optical isomer designation, such as poly(L(+) lactic acid), poly(d,l-lactic acid), poly(meso lactic acid) and the like.

Shaped forms of high molecular weight PLA, a functionally active ingredient and an excipient which have been processed into shaped forms are usually erratic in their rate of dissolution. Until the present invention it was believed that any polyester had to have a weight average molecular weight of at least 25,000 to be usable.

The scope of this invention is intended to include not only pharmaceutically active ingredients, excipients and additives singly, but also in combination with other pharmaceutically active ingredients, excipients and/or additives.

The following nonlimiting examples are presented to explain to one skilled in the art various embodiments of the invention.

Although the invention is exemplified in terms of theophylline as the functionally active ingredient, and lactose, dicalcium phosphate (DCP) or microcrystalline cellulose as the excipient and magnesium stearate as the lubricant, it will be clear to one skilled in the art that any suitable functionally active ingredient, excipient or lubricant may be employed. The dosage amount of a functionally active (pharmaceutically) ingredient can vary over a wide range depending on activity and time of sustained release. Generally 5% to about 60% of the tablet weight is functionally active ingredient. In the examples the tablets contained either 25% or 60% by weight functionally active ingredient.

The feed formulations were prepared by dissolving the polymer in methylene chloride and adding the solution to the blend of the pharmaceutically active ingredient and excipient. Subsequently, the organic solvent was removed by evaporation. After air drying of the granules a lubricant was added to the feed formulation and 500 mg tablets were formed by direct compression to about 5.5 kg to 6 kg of tablet hardness.

The physical properties of four batches of polylactic acid produced according to the above process and two commercial polycaprolactone (PCL-300 and PCL-700 grades of caprolactone of Union Carbide Corporation) samples are presented in Table I, Polymer Overview.

Dissolution studies were performed on the tablets in water at 37° C., using the USP XXI method 2. Paddle speed was 50 rpm. Samples of the dissolution medium were taken periodically and analyzed by UV spectroscopy (Beckman DU spectrophtometer) at a maximum wavelength of 270 nm for theophylline.

TGA Purity Determination

The TGA (200° C., isothermal, nitrogen) method of analysis of poly(d,l-lactic acid) follows: The changing slope of the thermogravimetric analyses (TGA) weight loss curve was calibrated to provide a measure of volatile (primarily lactide) impurity in the polymer product. The analysis showed polymer from Run C to be 97% pure, with about 2% of lactide present.

Glass Transition Temperature

The $T_G$, glass transition temperature, was determined using differential scanning calorimetry (DSC)

Weight Average Molecular Weight

Molecular Weight determinations were made using gel permeation chromatography. Unless specified otherwise weight average molecular weight is referred as $M_W$ while number average molecular weight is indicated by $M_n$. The ratio $M_W/M_n$ is the polydispersity index (PI).

EXAMPLE 1

Tablets were prepared as above consisting of 15% polymer, 60% theophylline and 25% excipient. Results are presented as Table II where "DCP" is dicalcium phosphate and "MCC" is Avicel microcrystalline cellulose. The polymers were ,-caprolactone (PCL-300), poly(DL-lactic acid) with a weight average molecular weight of 2,500 to 4,500 (DL-PLA) and poly(L-lactic acid) with a weight average molecular weight of 2,500 to 4,500 (L-PLA).

EXAMPLE 2

Tablets were prepared as in Example 1 consisting of 15% polymer, 25% theophylline and 60% excipient. Results are presented as Table III. The same abbreviations are employed as in Example 1 with the addition of HMW DL-PLA representing a commercial poly(DL-lactic acid) having a weight average molecular weight of over 30,000.

TABLE I
POLYMER OVERVIEW

|  | Mn | Mw | PI (Mw/Mn) | °C. Tc | % Lactide |
|---|---|---|---|---|---|
| A. Poly-(L-Lactic Acid) | 1,103 | 3,080 | 2.80 | 24 | >12 |
| B. Poly-(DL-Lactic Acid) | 1,100 | 3,150 | 2.86 | 26 | >12 |
| C. Poly-(DL-Lactic Acid) | 1,296 | 3,035 | 2.34 | 27 | 2.0 |
| D. Poly-(DL-Lactic Acid) | 1,804 | 3,852 | 2.14 |  | 2.5 |
| E. Polycaprolactone PCL-300 | 18,800 | 30,400 | 1.62 |  |  |
| F. Polycaprolactone PCL-700 | 47,000 | 90,700 | 1.94 |  |  |

TABLE II
PERCENT RATE OF DRUG RELEASE FROM 60% THEOPHYLLINE TABLETS CONTAINING 15% POLYMER AND 25% EXCIPIENTS

| Time Hr. | PCL-300 MCC | PCL-300 DCP | DL-PLA MCC | DL-PLA DCP | L-PLA MCC | L-PLA DCP |
|---|---|---|---|---|---|---|
| 0.5 | 14 | — | — | — | 23 | 8 |
| 1.0 | 20 | 13 | 47 | 14 | 35 | 12 |
| 2.0 | 27 | 19 | 73 | 32 | 44 | 16 |
| 4.0 | 40 | — | 94 | 42 | — | 25 |
| 6.0 | 47 | 33 | — | 48 | 66 | 32 |
| 12.0 | — | 47 | — | 57 | 83 | 46 |

TABLE III
PERCENT RATE OF DRUG RELEASE FROM 25% THEOPHYLLINE TABLETS CONTAINING 15% POLYMER AND 60% EXCIPIENTS

POLYMER/EXCIPIENT

| Time Hr. | PCL 300 MCC | PCL 300 DCP | DL-PLA MCC | DL-PLA DCP | L-PLA MCC | L-PLA DCP | HMW DL-PLA Lactose | HMW DL-PLA MCC | HMW DL-PLA DCP |
|---|---|---|---|---|---|---|---|---|---|
| 0.5 | 60 | — | — | — | — | — | — | — | — |
| 1.0 | 76 | 14 | 88 | 14 | 92 | 16 | 25 | 27 | 20 |
| 2.0 | 90 | — | 95 | — | 96 | 22 | 38 | 42 | 30 |
| 4.0 | 95 | 33 | — | 42 | 98 | 35 | 50 | 59 | 42 |
| 6.0 | 98 | 41 | 98 | 51 | — | 45 | 57 | 71 | 51 |
| 12.0 | 98 | 58 | — | 77 | — | 59 | 107 | 90 | 69 |

I claim:

1. A controlled release matrix dosage form comprising 1% to 75% by weight of a pharmaceutically active ingredient; 5% to 50% of a polymer of lactic acid; and 1% to 90% of an excipient selected from the group consisting of lactose, dicalcium phosphate, calcium sulfate, sugars, microcrystalline cellulose, gums, methylcellulose, starch, polyvinylpyrrolidone and clay; the polymer of lactic acid having a weight average molecular weight of about 2500 to about 4500 and containing less than about 4% lactide; and made by the steps of:
(a) heating lactic acid in a inert atmosphere to about 110° C. at approximately 101 kPa,
(b) advancing the temperature to about 120° C.,
(c) maintaining the temperature between about 120° and 140° at a pressure of about 80 kPa a sufficient time to remove about 52% of the theoretical amount of water, and subsequently advancing the temperature to 180° C. to 190° C. while reducing the pressure to about 10 kPa,
(d) maintaining the temperature and pressure at about 190° C. and 10 kPa for a time sufficient to remove about 92% of the residual water, and
(e) reducing the pressure to about 400 Pa while maintaining the temperature at least about 180° C. for a time sufficient to remove about 98% of the theoretical water and about 0.5% of the lactic acid as lactide to provide the poly(lactic acid) containing less than about 4% lactide.

2. A controlled release matrix dosage form of claim 1 wherein the excipient is selected from the group consisting of lactose, dicalcium phosphate, calcium sulfate, sugars, microcrystalline cellulose, gums, methylcellulose, starch, polyvinylpyrrolidone and clay.

3. The controlled release dosage form of claim 1 wherein the pharmaceutically active ingredient is selected from the group consisting of theophylline, quinidine sulfate, propanolol, chloropheniramine, testosterone and ethenyl estradiol.

* * * * *